United States Patent [19]
Greggs

[11] Patent Number: 4,473,353
[45] Date of Patent: Sep. 25, 1984

[54] METHOD FOR COSMETIC RESTORATION OF ANTERIOR TEETH

[75] Inventor: Thomas S. Greggs, Wheaton, Ill.

[73] Assignee: Greggs/Showalter, Wheaton, Ill.

[21] Appl. No.: 485,281

[22] Filed: Apr. 15, 1983

[51] Int. Cl.³ .............................................. A61C 5/00
[52] U.S. Cl. .................................................... 433/215
[58] Field of Search ........................ 433/215, 212, 199

[56] References Cited

U.S. PATENT DOCUMENTS

| | | | |
|---|---|---|---|
| 1,712,043 | 5/1929 | Limbarth | 433/215 |
| 3,004,343 | 10/1961 | Rydin | 32/13 |
| 3,422,535 | 1/1969 | Johnson | 32/12 |
| 3,468,028 | 9/1969 | Sunter | 32/12 |
| 3,986,261 | 10/1976 | Faunce | 32/12 |
| 4,129,946 | 12/1978 | Kennedy | 32/63 |
| 4,194,907 | 3/1980 | Tsai | 75/134 R |
| 4,210,447 | 7/1980 | Tsai | 75/171 |

FOREIGN PATENT DOCUMENTS 2078707 1/1982 United Kingdom .

OTHER PUBLICATIONS

Slocum, The Dental Digest, pp. 1-5, Oct. 27, 1924.
Rentz et al., Am. J. Orthod., pp. 499-510, Nov. 1973.
Bowen, Adhesive Bonding of Various Materials to Hard Tooth Tissues, JADA, vol. 74, pp. 439-445.
Rasmussen, J. Dent. Res., 57, (1), pp. 11-20, Jan. 1978.
Clinical Research Associates Newsletter, Oct. 1978, pp. 1 and 2.
Barkley et al., Dental Survey, Jan. 1979, pp. 22-23 and 25 and 27.
Raptis et al., JADA, vol. 99, Oct. 1979, pp. 631-633.
Hunt et al., Full Circle in Ceramics, vol. 1, No. 1, Feb. 1980, pp. 7-14.
Barkley et al., J. Ind. Dent. Assn., Sep./Oct. 1980, pp. 15-17.
Clinical Research Assn. Newsletter, Nov. 1980, pages, vol. 4.
Cammarato et al., Dental Clinics of North America, Apr. 1981, pp. 337-345.
Boyer et al., J. Dental Res., 61, (3), pp. 489-492, Mar. 1982.
Johnson, Pediatric Dentistry, vol. 4, No. 1, (1982), pp. 32-37.
Goteiner et al., Clinical Preventive Dentistry, Jan.-Feb. 1982, pp. 9-12.

*Primary Examiner*—Robert Peshock
*Attorney, Agent, or Firm*—Neuman, Williams, Anderson & Olson

[57] ABSTRACT

A method and article for the cosmetic restoration of anterior teeth is provided whereby a glazed porcelain labial veneer is custom-made for a patient's tooth and thereafter chemically and mechanically bonded to such tooth, so as to provide a healthful and long-lasting cosmetic restoration of desired color, shape and esthetic appearance.

7 Claims, 12 Drawing Figures

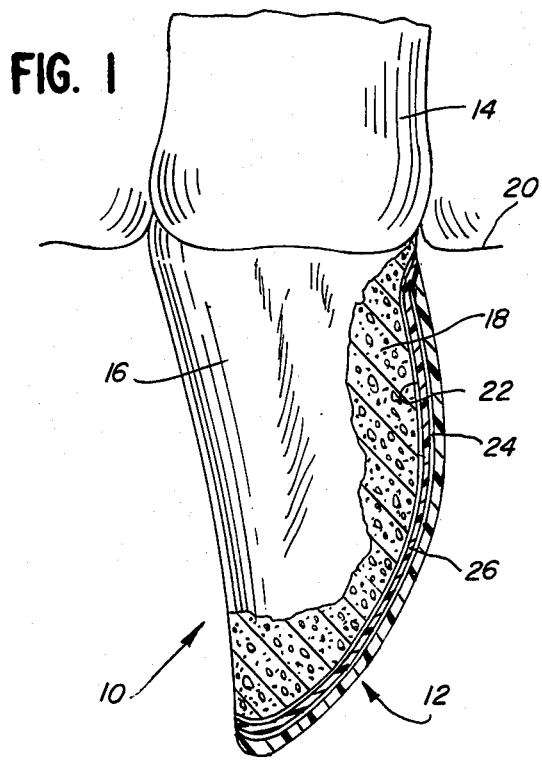
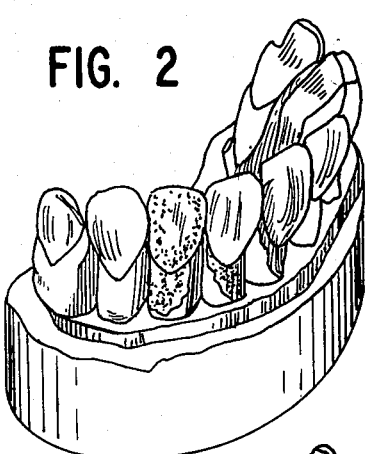
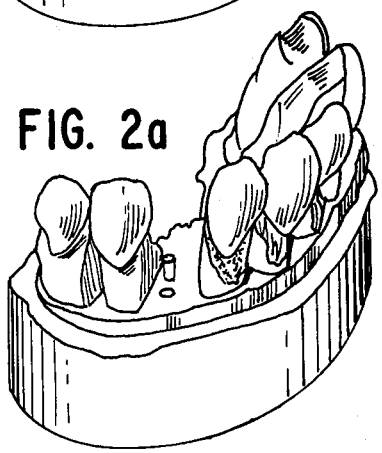
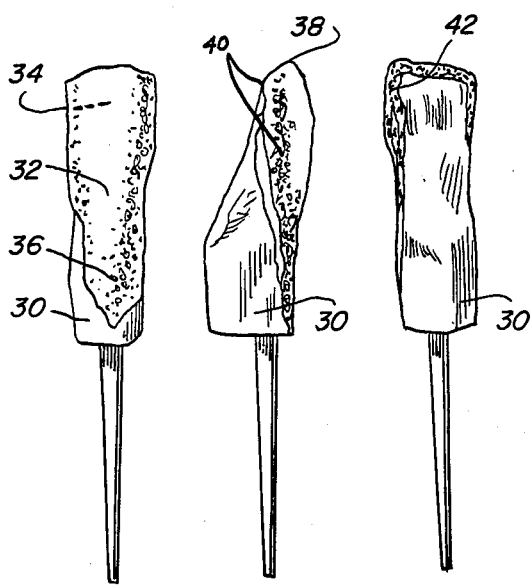
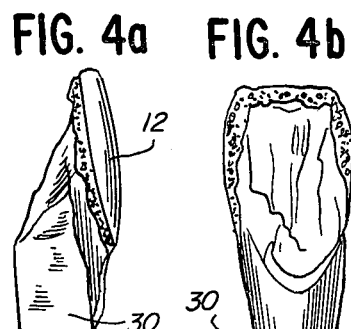
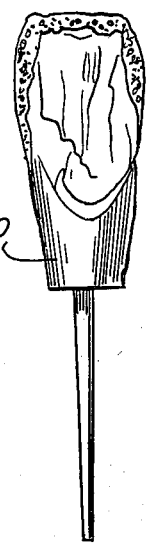
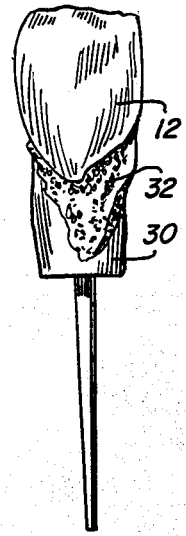
FIG. 1 FIG. 2 FIG. 2a FIG. 3a FIG. 3b FIG. 3c FIG. 4a FIG. 4b FIG. 4c

METHOD FOR COSMETIC RESTORATION OF ANTERIOR TEETH

FIELD OF THE INVENTION

This invention relates generally to veneer restoration of anterior teeth to eliminate cosmetically unacceptable defects such as discoloration or hypoplasia. More particularly, the invention relates to the fabrication and application of a custom-made glazed porcelain labial veneer adapted to be chemically bonded to the appropriate enamel surfaces of a person's cosmetically defective tooth and so fabricated as to provide a long-lasting biocompatible dental restoration of desired color, shape and esthetic appearance.

BACKGROUND OF THE INVENTION

The dental practitioner is familiar with a host of cosmetically unacceptable facial aspects of anterior teeth. These aspects include discoloration due to pharmaceuticals, diet, metabolic disease or bacteria; and can also include enamel defects or hypoplasia.

Until recent years, cosmetic restoration of such discolored teeth could be effected only by application of crowns. These crowns are composed of expensive metal materials, such as gold, or of plastic materials and necessitate a considerable amount of dental chair time for their application. Moreover, because crown application frequently requires drastic reduction or reshaping of an affected tooth, it is contraindicated in many situations, especially for patients of young age.

A more recently utilized cosmetic restoration technique has been to apply a layer of acrylic or composite resin directly to the etched enamel surface of the tooth and then light cure the resin to bond it to the tooth. The resulting laminate can be shaped, contoured and given its appropriate anatomy with composite finishing burs, stones and discs. Application of direct composite resin laminates is time consuming and has been found ineffective in cases of severe tooth discoloration where it has not been possible to mask completely.

It is also known to use preformed acrylic laminates which are prepared in a laboratory or to commercial specifications, and are then fitted to the affected teeth in the dental chair. One such restoration system involves fabricating an acrylic laminate in a laboratory, in much the same manner as described above, on a mold of the affected teeth. Because the laminates can not be fitted to adjacent teeth on the mold, this process requires that two separate molds be provided to the lab technician. Additionally, the process is time consuming. Discoloration of the tooth is masked by mixing shade resin with the bonding material.

A second type of preformed laminate is provided by the L.D. Caulk Company in its Mastique kit. Each kit contains a full selection of pre-sized plastic laminates and accessories, including bonding resins. The Mastique laminates are bonded to acid-etched enamel tooth surfaces using light cured bonding resins. They may be prepared in the dentist's office or in advance on a model in the laboratory. A disadvantage of the Mastique system is that the laminates themselves have little color or shade; thus, all shading must be effected through the shade and bonding resins. Such shades have been known to change over a short period of time. It is also more difficult to control the shade of the restoration at various areas of the labial surface. It is known, for example, that dark tooth discoloration is often most intense in the gingival area of the tooth.

While the aforementioned restorative techniques have achieved some satisfactory results, they are not altogether desirable. Because of the porosity of the plastic materials from which these laminates are made, their long-term color stability and wear resistance are low. The thickness of these laminates has also been a source of periodontal pathology development such as inflammation of the gingival tissue. Additionally, the plastic materials have been found to be toxic to the mouth. Other problems reported with respect to these techniques have included extended dental chair time, inadequate marginal finish and contour and lack of cosmetic customizing and transparency. It is desirable, therefore, to provide a long-lasting, non-pathogenic custom-made veneer of specified color, shading and shape, which is easily suited for inexpensive and effective adaptation to a dental patient's cosmetically defective teeth.

SUMMARY OF THE PRESENT INVENTION

It is an object of the present invention to overcome the deficiencies experienced with prior dental restoration techniques. More specifically, it is an object to provide a method and article for long-term cosmetic restoration of anterior teeth which is simple in fabrication and application, while being superior to prior art restorations with respect to cost, quality, patient benefit and healthful reliability.

It is another object of the present invention to provide a custom-made glazed porcelain labial veneer adapted to be chemically bonded to the appropriate enamel surfaces of a patient's natural tooth and so fabricated to provide a durable, long-lasting and functional tooth restoration of desired color, shape and overall esthetic appearance.

It is still another object of the present invention to provide a thin veneer for tooth restoration which does not promote inflammation of the gingival tissue and which is otherwise well received by, and suitably adapted to, the oral environment so as to avoid periodontal pathology development or deterioration or discoloration of the veneer itself.

It is yet another object of the present invention to provide a cosmetic tooth restoration that may be simply and efficiently accomplished in a short period of time without necessitating use of anesthesia or restructuring of the tooth to be restored.

It is also an object of the present invention to provide a glazed porcelain veneer which is custom-made for optimal fit and cosmetic characteristics, including accurate coloring and long-term color stability.

It is an even further object of this invention to provide a method of restoring cosmetically defective teeth that may be simply effected through the use of low cost materials which can be made available in kit form to dentists and laboratory dental technicians.

These and other objects of the invention will be apparent hereinafter from the specification which describes the best mode of practicing the invention as currently known and a preferred embodiment. Reference should also be made to the drawings, which constitute a part of the disclosure, and the subject matter claimed.

Generally, the objects of the present invention are accomplished by a custom-made porcelain labial veneer adapted to be bonded directly to the enamel surface of a patient's tooth, and the laboratory and clinical techniques associated with fabricating and applying such a veneer. The objects are also accomplished, in large part, by applicants' innovative use of non-porous glazed porcelain in a resin bonding application rather than acrylic laminates or direct bonding composite materials, such use having heretofore been considered unworkable because of porcelain's unpredictable tendency to fracture without the added strength of a metal substructure.

In accordance with the present invention, a dental patient having cosmetic defects will first schedule an impression and record appointment with his or her dentist. The dentist uses conventional crown and bridge impression materials to prepare a model of the patient's teeth and further records data pertaining to bite, shade and so forth. Since patients having gross cosmetic defects often require orthodontic intervention, cross consultation with an orthodontist may be necessary. The initial impression and record appointment involves a chair time of approximately forty-five minutes, after which the models and records are sent to the dental laboratory for veneer fabrication.

The lab technician pours the impressions with die stone and prepares a Pindex model, pinning all teeth to be veneered as well as adjacent teeth. Each tooth die is then undercut at the cervical extension, trimmed at the marginal areas of the regions to be veneered and hardened, so as to replicate the identical structure of the cosmetically defective tooth. A triangular-shaped platinum foil is placed over the labial surface of the tooth die with the apex pointing downward and forming a tab portion which extends below the gingival margin. The base of the triangular-shaped foil is folded over the incisal edge of the die and at least partially around the proximal surfaces in such a manner as to form a snugly fitting, but hingedly removable at the top, foil sheath on the die. For added retention, the foil is adhered to the previously made undercut.

The platinum matrix so formed is removed from the die by grabbing the tab portion formed by the foil apex and pulling the foil sheath hingedly off of the incisal edge of the die. The matrix is then held over a bunsen burner flame to decontaminate it and it is reapplied to the die and burnished thereon.

Porcelain is then applied to the labial surface of the platinum matrix using a brush, starting at the cervical undercut and working up to the incisal edge. The buildup of porcelain is made thinly and uniformly. The foil matrix is again removed from the die, and placed on a tray for firing the porcelain according to specifications. The matrix and baked porcelain veneer thereon are then replaced onto the die where the marginal areas of the veneer are finished, the veneer is then contoured into an esthetic shape and the labial anatomy is carved.

The veneer and matrix are then removed for the last time, the veneer is cleaned ultrasonically and is stained and glazed using conventional techniques to conform to the shade characteristics and requirements set forth in the patient's dental record. The room temperature veneers are placed in distilled water for one minute and the foil is gently removed from the porcelain veneer with tweezers. The entaglio, or inside surface of the veneer is etched, usually by air abrasion, to promote bonding thereof to the enamel tooth surface. The result of this technical procedure is the fabrication of a custom-made glazed porcelain labial veneer adapted to conform to and be bonded to the labial enamel surface of a cosmetically defective tooth.

The cosmetic restoration is completed with a placement appointment in which the dentist applies the custom-made porcelain veneer to the tooth. The appropriate enamel surfaces of the tooth are etched with an acid solution, preferably in a gel formulation, to create micropores and thereby promote bonding. The acid gel etchant should be applied no less than four and no greater than six minutes. Once the tooth is so prepared, the entaglio is coated with a thin layer of light-curing bonding agent. A similar layer is applied to the etched enamel bonding surface of the tooth. Both layers are polymerized by light curing. A coating of dental filler material is then applied to either the tooth or the entaglio of the veneer, and the veneer is then placed onto the tooth. Excess filler material is trimmed away and the filler material is polymerized by a second application of light. The dentist then finishes the proximal and incisal margins to provide a smooth restoration surface.

It can readily be seen that this simple and highly effective dental restoration technique can be easily learned by clinicians and technicians as well. Moreover, the materials utilized in this technique are susceptible to distribution in kit form both to the dentist and the laboratory. Thus, this superior restorative technique can readily and inexpensively be made available to its numerous potential beneficiaries.

Clinicians may find the above-described restoration technique desirable in the closure of diastemas and the gross recontouring of congenitally malformed teeth. Such decisions are within the discretion and good judgment of the dentist and should be predicated on the patient's particular oral hygiene and dental situation. Contraindications to the use of veneers generally include edge-to-edge bite, high caries rate, occlusal interference and oral habits such as bruxism.

From the description thus far provided, it is apparent that the proposed method and article for cosmetic restoration of anterior teeth may be used in a number of applications advantageously over such restoration techniques as are known in the art.

BRIEF DESCRIPTION OF THE DRAWINGS

For a more complete understanding of the invention, reference should be made to the drawings, briefly described below:

FIG. 1 is a side elevational view of an anterior tooth showing a portion of the enamel thereof and a custom-made porcelain labial veneer bonded thereto.

FIGS. 2–2a show a stone die of a patient's anterior teeth and illustrate a foil matrix burnished on a tooth die, alone and with a porcelain veneer baked thereon.

FIGS. 3a–3c show front, side and rear views of a foil-sheathed stone tooth die such as would be removed from and inserted into the die of FIGS. 2–2a.

FIGS. 4a–4c show side, rear and front views of a foil-sheathed stone tooth, as in FIGS. 3a–3c, with a porcelain veneer baked thereon.

DESCRIPTION OF THE PREFERRED EMBODIMENT

Figure 5:
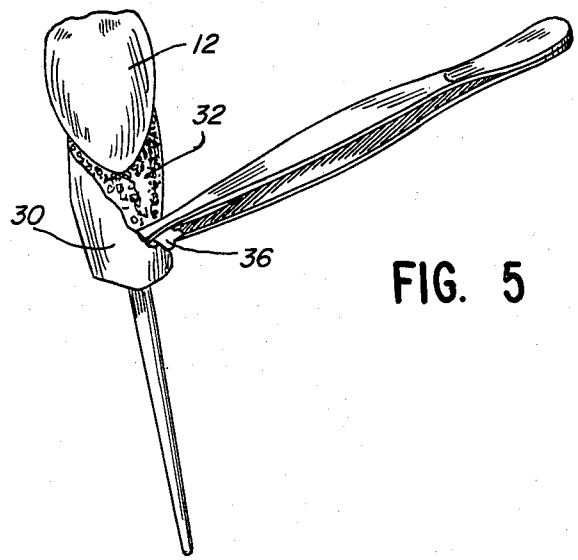
FIG. 5 illustrates the technique for removing the foil matrix off of the stone tooth die.

Referring now to FIG. 1, an anterior incisal tooth 10 is generally illustrated with a custom-made porcelain labial veneer 12 bonded thereto to effect a cosmetic restoration thereof. Tooth 10 is shown to have a root portion 14 and a crown portion 16, with the crown portion 16 having an enamel coating or surface 18. The root portion 14 and crown portion 16 are shown positioned relative to the gingival margin 20.

Similarly to the application of acrylic laminate restorations, labial veneer 12 is bonded to tooth 10 without drastic reduction or reshaping of the tooth. After the color, shade and shape of tooth 10 have been ascertained and incorporated into the esthetically and physically desirable labial veneer 12, the receiving tooth 10 is prepared for affixation. The appropriate enamel surfaces of the tooth are etched with an acid solution, such as a solution of 50–75% phosphoric acid, to increase adhesion of the acrylic restorative bonding materials. It has been found that an acid gel formulation is easier to work with and further that an optimal enamel bonding surface is obtained when such gel is applied no less than four and no greater than six minutes. This time will vary, of course, with the selected acid concentration.

The acid-etched enamel surface 18 of tooth 10 is then coated with an acrylic bonding agent in order to seal the micropores therein created by the etching and to establish a bonding surface 22 on the tooth 10. It is preferable to use a light-cured bonding resin because such resins are capable of controlled polymerization, thus permitting the clinician to take his time and inspect the bonding surface prior to application of the labial veneer 12. Although there are a number of bonding agents which are suitable for this application, as will be appreciated by those skilled in the art, it has been found desirable to use a visible light-cured unfilled bonding resin (e.g., Prisma-Fill) that is compatible with the dental filler material hereinafter described and used in the practice of this invention. A bonding surface 24 is similarly formed on the entaglio of labial veneer 12, which has been previously etched during fabrication. Bonding surfaces 22 and 24 are then polymerized by application of visible light.

A coating of dental filler material 26, such as for example, Prisma-Fill (a small size composite resin) or Silux (a microfill resin), is then applied to either of bonding surfaces 22 or 24 and the labial veneer 12 is press-fit to the labial face of tooth 10 for which it was custom-made. The entaglio of labial veneer 12 is thereby filled, removing any interstices between bonding surfaces 22 and 24 of tooth 10 and labial veneer 24, respectively. The excess dental filler material 26 is trimmed away and the filler material is polymerized by a second application of visible light. Lastly, the clinician finishes the marginal edges of the labial veneer 12, as by lightly sanding, to provide a smooth restoration surface.

So applied, the custom-made porcelain labial veneer 12 provides a thin and long-lasting tooth restoration which is superior to prior art acrylic laminate restorations and is non-pathogenic and non-toxic in the oral environment.

Referring now to FIGS. 2–7, a method will be demonstrated for fabricating the custom-made porcelain labial veneer, in accordance with the present invention, described above and shown bonded on a tooth in FIG. 1. After the dentist transmits the necessary models and records to the lab technician, a die is prepared for each affected tooth for which a veneer must be custom-made. Referring to FIGS. 2–2a, a stone die of a patient's anterior teeth is shown made into a Pindex model 28, with the teeth to be veneered and the adjacent teeth thereto pinned for removal and replacement. Moreover, each individual stone tooth die is trimmed at its marginal areas and undercut at its cervical extension to replicate the identical structure of the corresponding natural tooth. Once the Pindex model is prepared, each affected tooth is fitted with a porcelain labial veneer.

Referring particularly to FIGS. 3a–3c, a stone tooth die 30 is shown removed from the Pindex model 28 and having a foil sheath or matrix 22 burnished thereon. The foil matrix 32 is formed from a platinum foil. It has been found desirable to use a trangular-shaped foil, placing it over the labial surface 34 of the die 30 with the apex pointing downward and forming a tab portion 36, which extends below the gingival margin. The base of the triangular-shaped foil is folded over the incisal edge 38 of die 30 and around the proximal surfaces 40 to grip the lingual surface 42 of die 30. The foil is then pressed against the die 30 at the previously made cervical undercut, to increase retention, and burnished on the die to form the snugly fitting foil matrix 32. Importantly, the foil matrix 32 is hingedly removable from die 30 about incisal edge 38 by lifting tab portion 36 outwardly and upwardly from the face of die 30. It may be desirable at this stage to so remove the foil matrix 32 and hold it over a flame to decontaminate it prior to the porcelain application.

Porcelain is then applied to the labial surface of the foil matrix 32. It has been found desirable to brush the porcelain powder onto the foil matrix 32 starting at the cervical undercut and working up to the incisal edge to insure thin and uniform application thereof. Once again, the foil matrix 32 is hingedly removed from the die 30, as previously described, and placed on a tray for firing according to specifications. It will be appreciated that a number of porcelain compounds may be used within the spirit and scope of this invention.

The foil matrix 32 and baked porcelain veneer 12 thereon are then replaced onto die 30, where the marginal areas of the veneer are finished and the veneer is contoured into an esthetic shape. This finishing work is performed on die 30, shown with foil matrix 32 and porcelain veneer 12 in FIGS. 4a–4c, and with reference to the Pindex model 28 shown in FIGS. 2 and 2a.

Referring to FIG. 5, the above-described method of separating the foil matrix 32 from the die 30 is shown, this time with the finished veneer 12 affixed to the foil matrix 32. The veneer 12 and foil matrix 32 are removed a last time, after which the veneer is cleaned ultrasonically.

The porcelain veneer 12 is then stained and glazed, using conventional techniques, to conform identically to the physical and desired esthetic characteristics of the affected tooth. This coloring and shading technique is obviously far more accurate and predictable than heretofore known in connection with acrylic laminate restorations.

Figure 6:
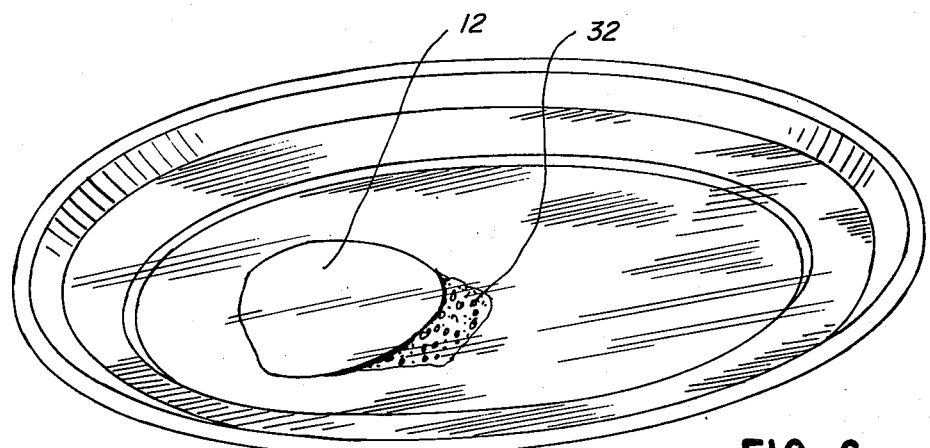
FIG. 6 illustrates the technique for separating the foil matrix from the porcelain veneer.

FIG. 6 illustrates one method of separating the finished, custom-made porcelain labial veneer 12 from the foil matrix 32. While other means may be employed within the spirit and scope of this invention, it has proven effective to place the room temperature veneer and matrix into distilled water for approximately one minute and thereafter gently remove the foil matrix 32 from the porcelain veneer 12 with tweezers.

Figure 7:
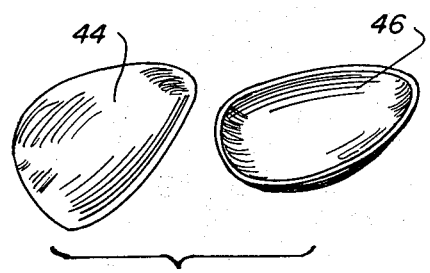
FIG. 7 shows the anterior veneer surface and the entaglio portion of a custom-made porcelain labial veneer fabricated according to the present invention.

FIG. 7 shows the anterior veneer surface 44 and the posterior concave veneer surface or entaglio 46 of a custom-made porcelain labial veneer fabricated according to the present invention. It has been found to promote a bonding to tooth 10 when the entaglio 46 of veneer 12 is etched, such as by air abrasion with 50 micron aluminous oxide. Another method of etching the entaglio 46 of veneer 12 is to apply a mesh to die 30 prior to application of foil matrix 32, resulting in a grid-like foil surface and a corresponding grid-like entaglio of the porcelain veneer.

It is believed that the embodiments herein illustrated and described accomplish all of the above enumerated objects and have made apparent a number of modifications which can be made in the invention disclosed by those having the benefit of the foregoing teachings without departing from the spirit and scope of these principles. Accordingly, it is intended that this invention be limited only by the scope of the appended claims.

What is claimed is:

1. A method of fabricating a custom-made porcelain labial veneer for a tooth which comprises:
   preparing, from an impression of the patient's teeth, a die having a portion of identical configuration as such tooth and using a round burr to undercut the die at the cervical extension and to expose the marginal areas of the labial, gingival and interproximal regions to be veneered;
   placing a metal foil over the labial surface of said die such that a tab portion of said foil extends below the gingival margin thereon and tightly folding said foil over the incisal edge and at least partially around the proximal surfaces of said die so as to form a snugly fitting, but hingedly removable at the top, foil sheath on said die;
   burnishing said foil sheath;
   applying porcelain powder to the labial surface of said foil-sheathed die to build a thin veneer conforming to the shape of the bonding surface of such tooth;
   removing the foil sheath and porcelain veneer affixed thereto from said die by gently pulling said tab portion away from the labial face of said die and lifting said tab portion so as to cause said foil sheath to hinge about the incisal portion and lift off of such die;
   firing the porcelain veneer on said foil sheath;
   replacing the foil sheath and porcelain veneer affixed thereto onto said die and finishing the marginal areas of said veneer;
   removing the foil sheath and porcelain veneer affixed thereto from said die again and staining and glazing the veneer to achieve the desired cosmetic restoration appearance;
   separating said foil sheath from said porcelain veneer to provide a custom-made porcelain labial veneer.

2. A method of fabricating a custom-made porcelain labial veneer, as recited in claim 1, including the additional step of:
   applying a mesh to said die prior to application of said foil thereon.

3. A method of fabricating a custom-made porcelain labial veneer, as recited in claim 1, including the additional step of:
   removing said foil sheath prior to application of the porcelain, heating said foil sheath to decontaminate it and replacing it on said die.

4. A method of fabricating a custom-made porcelain labial veneer, as recited in claim 1, wherein said foil is made of platinum.

5. A method of fabricating a custom-made porcelain labial veneer, as recited in claim 1, wherein said foil is separated from said porcelain veneer by placing the foil sheath and porcelain veneer affixed thereto in water and gently pulling said foil away from said porcelain veneer with tweezers.

6. A method of placing a custom-made porcelain labial veneer on a patient's cosmetically defective tooth which comprises:
   providing a custom-made porcelain labial veneer;
   etching appropriate portions of the labial, proximal and incisal enamel surfaces of such tooth with an acid solution to create micropores therein;
   applying a thin layer of bonding agent to both the etched enamel bonding surface of the tooth and the posterior concave bonding surface of said veneer, and light curing said bonding agent;
   applying dental filler material to said posterior concave bonding surface, placing said veneer accurately onto such tooth, trimming away excess filler material and light curing said dental filler material; and
   finishing the proximal and incisal margins to provide a smooth tooth restoration surface.

7. A method of placing a custom-made porcelain labial veneer on a patient's cosmetically defective tooth which comprises:
   providing a custom-made porcelain labial veneer;
   etching appropriate portions of the labial, proximal and incisal enamel surfaces of such tooth with an acid solution to create micropores therein;
   applying a thin layer of bonding agent to both the etched enamel bonding surface of the tooth and the posterior concave bonding surface of said veneer, and allowing said bonding agent to cure;
   applying dental filler material to said posterior concave bonding surface, placing said veneer accurately onto such tooth, trimming away excess filler material and allowing said dental filler material to cure; and
   finishing the proximal and incisal margins to provide a smooth tooth restoration surface.

* * * * *